US00PP13486P2

(12) United States Plant Patent
Bowden et al.

(10) Patent No.: US PP13,486 P2
(45) **Date of Patent: *Jan. 21, 2003**

(54) BASIL PLANT NAMED 'MAHA'

(75) Inventors: Donald R. Bowden, Oceanside, CA (US); Paul W. Friedman, Encinitas, CA (US)

(73) Assignee: Herb Thyme Farms, Inc., So. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/129,027

(22) Filed: Aug. 4, 1998

(51) Int. Cl.[7] ..... A01H 5/00
(52) U.S. Cl. ..... Plt./258
(58) Field of Search ..... Plt./258, 259

(56) References Cited

PUBLICATIONS

Bown, D. The Herb Society of American Encyclopedia of Herbs and Their Uses. 1995, New York:DK Publishing. pp. 166–167.*

* cited by examiner

*Primary Examiner*—Bruce R. Campell
*Assistant Examiner*—Wendy Couchoud Baker
(74) *Attorney, Agent, or Firm*—Foley & Lardner; Bernard L. Kleinke

(57) ABSTRACT

A new and distinct variety of a basil plant substantially as herein shown and described, characterized as to novelty by increased resistance to Fusarium wilt, a larger leaf, increased shelf life, and increased productivity.

2 Drawing Sheets

BACKGROUND OF THE INVENTION

The present invention is a new and distinct basil plant.

Basil (*Ocimum basilicum*) is a popular herb having cooking and medicinal uses. In cooking, the herb is often used either fresh or dried to impart its distinctive flavor into various dishes, especially Italian cuisine. The most common types of basil for cooking purposes are the Sweet Italian basil varieties. As an herbal medicine, basil is believed to have a soothing effect on the digestive system.

Basil is commonly used in cooking in either a fresh or dried form. Recently, the demand for fresh basil has greatly increased. Not only has there been a general trend in cooking to use fresh ingredients, but modern cooks are discovering the taste advantages of using fresh herbs such as basil. As with the sale of any harvested fresh plant, visual appeal and fresh characteristics are important to obtain maximum commercial value.

Sweet Italian basil is an annual plant that is generally planted for a single harvest season. Each year, therefore, a new crop of Sweet Italian basil is typically seeded. Sweet Italian basil is particularly susceptible to the disease, Fusarium wilt. Fusarium wilt is characterized by damping-off, collapse of the plant, wilting, and a brown dry rot. This disease is caused by any of several fungi of the genus, Fusarium. Fusarium wilt can devastate a stand of basil and there is no known effective remedy. Therefore, if a stand of basil is attacked by Fusarium wilt, the stand is harvested at dramatically reduced levels. Once a stand is infected with Fusarium wilt, a die off of about 70% is typical, thus dramatically reducing the economic value of the crop.

When fully grown, the Sweet Italian basil plant may reach a height of two feet. The plant has green shiny 1–2 inch long leaves and has spikes of white flowers. During its growth period the Sweet Italian basil plant is also susceptible to attack by pests. Particularly problematic is the root knot nematode. The root knot nematode is an unsegmented worm such as the round worm, and attacks the root system of the Sweet Italian basil. Although not as devastating as Fusarium wilt, the root knot nematode has a significant negative effect on the production levels of that crop.

Sweet Italian basil, being an annual, is generally grown for only a single season and can commonly be harvested eight to ten times. Each time a basil plant is harvested, only selected parts of the foliage are removed for processing and sale. The harvested parts of the basil plant are commonly referred to as "basil tops", even though the harvested parts do not necessarily come only from the top of the plant.

Commercially harvested sweet basil requires careful monitoring of temperatures for optimal production. For example, once temperatures reach approximately 100 degrees, there is a dramatic effect on the turgidity of the cell walls of the plant, causing rapid wilt. Therefore, a commercial basil grower must delay harvesting until more moderate temperatures return, or accept the risk that a substantial amount of the basil harvested in high heat will wilt and have to be discarded.

Once the basil tops have been harvested, they are refrigerated and packaged. The refrigerated packages are shipped to commercial market outlets where they are sold. Once the basil tops have been harvested from the Sweet Italian basil plants, the basil tops can deteriorate rapidly by wilting and turning black. Within a few days after harvesting, the harvested basil tops typically have deteriorated to the point they are no longer fit for sale. Once the basil has deteriorated beyond a point of marketability, it must be discarded by the commercial outlet, thereby being a total economic loss. Sweet Italian basil typically must be sold within only four days after harvest.

The productivity of basil is measured in the pounds of basil tops harvested per acre each month. Since fresh basil is sold by weight, the productivity of a crop of basil is therefore a primary indicator of the economic value for a particular variety. In the peak summer growing season, it is possible to get up to 9,250 pounds per acre per month from a crop of Sweet Italian basil. This productivity drops dramatically to about 3900 pounds per acre per month in the cooler winter months.

Once the growing season has ended, the basil plants are removed and new plantings are grown for the succeeding season. Although typically a crop of Sweet Italian basil is planted from seed, in some rare circumstances, it may be desirable to asexually propagate Sweet Italian basil. However, the Sweet Italian basil plant can be difficult to propagate asexually in quantity as asexually propagated basil plants typically die off at a rate exceeding 60%.

BACKGROUND OF THE PLANT

As indicated, the present invention relates to a new and distinct variety of basil, named 'Maha'. 'Maha' has been successfully asexually reproduced by the above-listed inventors since the spring of 1994. For the planting season 1993, a crop of basil was propagated by seed. At the end of the 1993 growing season, certain plants were selected for their unique characteristics, including not-seen-before resistance to Fusarium wilt. These 1993 stock plants were isolated from the remaining crop. In 1994, a single plant was selected for continued propagation. Over the next few successive planting seasons, cuttings were taken and asexually propagated to increase the number of new basil plants. Throughout this process the plants were identified and segregated from the traditional Sweet Italian basil.

Specially, the asexual reproduction of 'Maha' was accomplished by taking softwood cuttings from a strong apical part of the stock new basil plant. The cuttings were at least five inches in length and were chosen such that there was no discoloration in the stem or leaf. Although branch stems are not preferred, they could be used if necessary to increase the number of plants. The cuttings were occasionally misted to maintain their freshness. Immediately prior to planting in the flats, the cuttings were cut back to about a three inch length, thereby reducing the amount of moisture loss caused by the cut. If the leaves of the cutting were excessively large, they were trimmed. A new fresh angled cut was made on the cutting, a rooting hormone applied, and the cutting inserted into soil in a flat.

Once the cutting was in the soil medium, it was neccessary to dampen immediately. Care was taken that the soil was tightly placed against the cutting, thereby reducing the air space around the cutting and increasing the contact between the soil and the plant material. Flats having the newly planted cuttings of the new plant were maintained at approximately 80° F., thereby allowing for rapid root development. Frequent and short waterings were given to maintain proper moisture levels. As the roots began to develop, the watering frequency was decreased. Although adequate water is important in the asexual propagation process, care was taken not to over water.

The time necessary for the cuttings to mature into transplantable plants varied depending on the season and temperature. In summer, the cuttings went from cutting to plantable plant in only 7 to 10 days, and this period would extend to 14 to 21 days in winter.

DETAILED DESCRIPTION OF THE PREFERRED EMBODIMENTS

Figure 1:
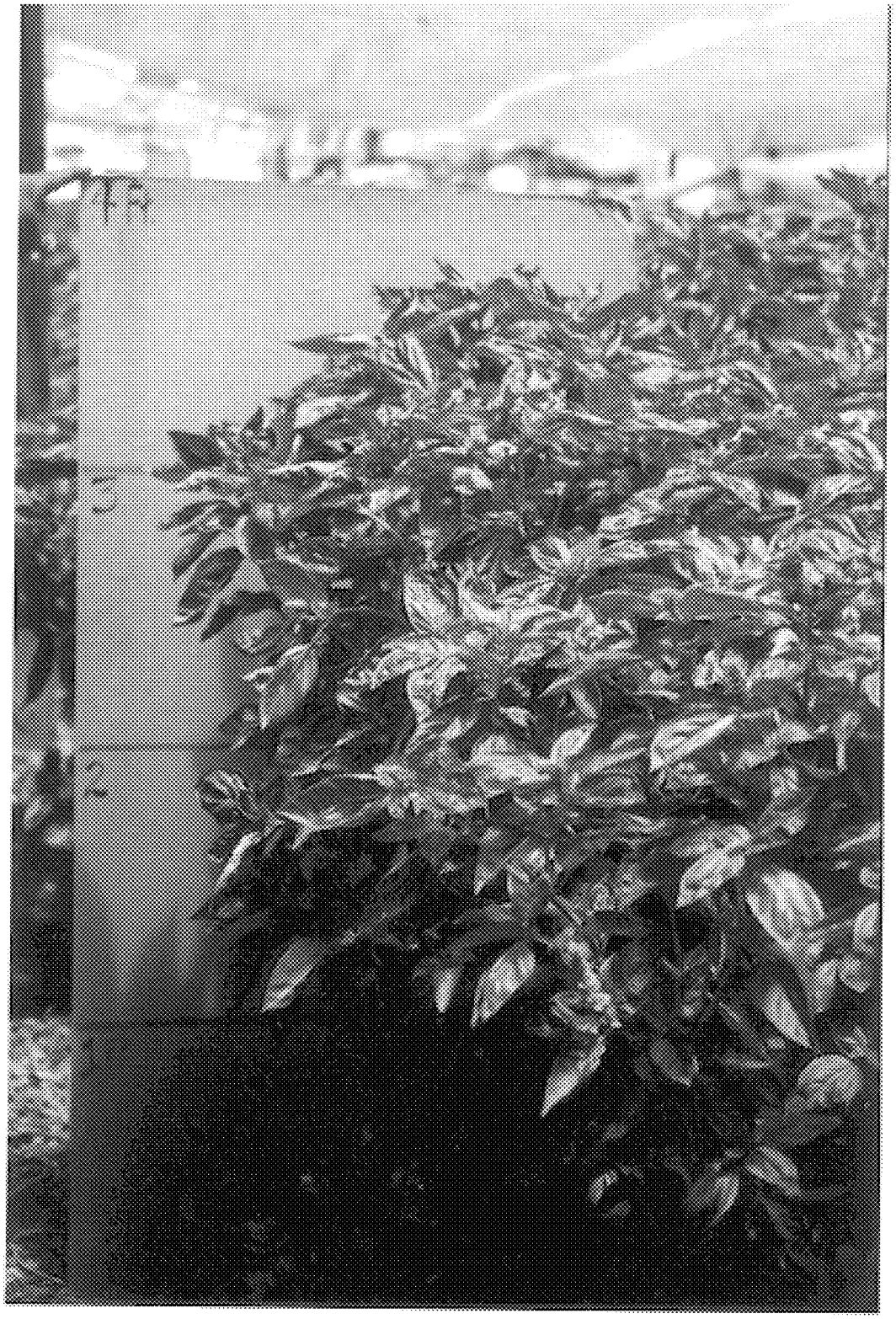
FIG. 1 of the accompanying photographic drawing illustrates 'Maha', the color being as nearly true as possible with color illustrations of this type. 'Maha' is shown with a background having 1 foot segmentation for size reference.
Figure 2:
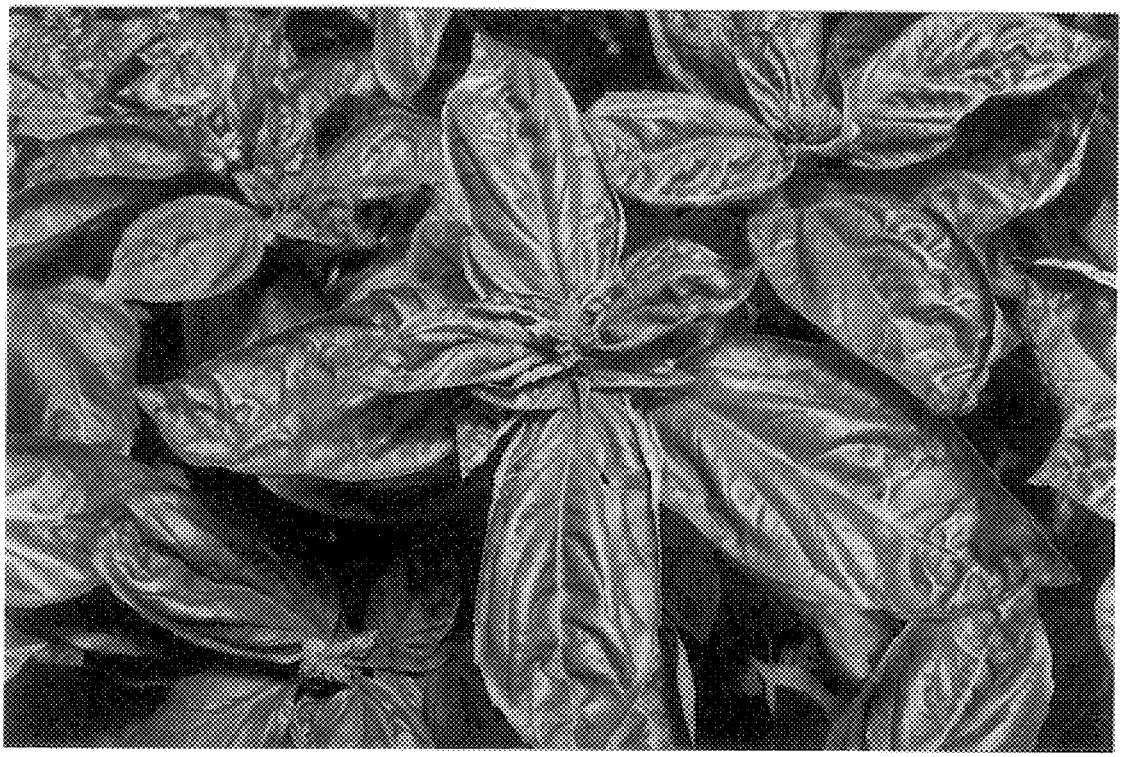
FIG. 2 of the accompanying photographic drawings illustrates a close-up view of the top of 'Maha' showing leaf ribbing and texture, the color being as nearly true as possible with color illustrations of this type.

A detailed description of 'Maha' is as follows based upon observation made from the plants grown in Oceanside, Calif. 'Maha' was grown and asexually reproduced from the spring of 1994 until July of 1998. 'Maha' has been found to retain its distinctive characteristics through successive asexual propagation.

'Maha' is particularly easy to asexually reproduce. As indicated above, the new basil plants matured from cuttings to transplantable plants in only 7–10 days in the summer and 14–21 days in the winter. Indeed, the plants could be rooted in less than seven days if temperatures were consistently held between 75 and 90 degrees, and even at 65 degrees the plants could be replanted in only 14 days. Not only was the asexual reproduction faster due to the quick rooting characteristics of 'Maha', but 'Maha' had a survivability rate of approximately 90%. Since known types of basil have a survivability rate of only approximately 40%, an additional 50% of the cuttings survived from the cutting stage to the rooted stage. Therefore, 'Maha' exhibits an ease of asexual reproduction not seen in prior plants.

'Maha' also exhibits dramatically increased resistance to the devastating Fusarium wilt disease. When under attack by Fusarium wilt, a crop of 'Maha' has a die off of typically less than 10%. This is in sharp contrast to the 70% die-off expected of known sweet Italian basil varieties. Further, 'Maha' exhibits increased resistance to pests, primarily to the root knot nematode. Due to its resistance to disease and pests, more of the rooted plants survive to maturity and are therefore available for harvest.

'Maha' has been shown to produce a plant at an overall height of between two and a half to four feet. This is nearly a full foot taller than typical varieties of Sweet Italian basil. Further, the leaf-to-stem ratio is particularly high on 'Maha'; thereby providing more harvestable plant material per stem.

Indeed, 'Maha' exhibits harvestable productivity levels approximately twice the productivity of known Italian Sweet basil. For example, in summer 'Maha' produces approximately 19,300 pounds per acre per month, and in winter, can produce approximately 8,950 pounds per acre per month. Thereby the economic value of a stand of 'Maha' is at least twice as valuable as a stand of typical Sweet Italian basil.

This increase in productivity is due to several factors. First, as discussed above, 'Maha' is larger and has a better leaf to stem ratio than prior plants. Also, the increased resistance to disease and pests results in stronger more productive plants. Most significantly, 'Maha' grows much faster than prior plants. Indeed, rather than having eight to ten harvests as normally expected, 'Maha' is harvested anywhere from 15 to 25 times a season, with decreased harvesting intervals. Further, 'Maha' does not have to be grown as annual, but may produce season to season. Therefore, the mature 'Maha' plant has a dramatically longer period where it yields at a higher economic level.

Also contributing to the increased productivity is the increased leaf size of 'Maha'. The leaf size of the mature new basil plant is 3–4 inches in length. The color of the upper side of the leaf is a light dark green to medium dark green, which is darker than the typical sweet Italian basil plant.

Further contributions to the increased productivity is the extended temperature range where 'Maha' produces at an acceptable economic level. For example, 'Maha' withstands temperatures down to 50° F. and still produces acceptable commercial yields. Even more dramatic is that 'Maha' provides exceptional production yields at temperatures exceeding 110° F.

Not only does 'Maha' produce well at these high temperatures, but it also has improved wilt resistance in high temperatures. Basil tops harvested in temperatures over 100° F. have exhibited substantially reduced wilting as compared to a typical basil plant. Indeed, no appreciable wilt is observed even at temperatures of 110° F.

Upon harvest, the basil tops taken from the new plants exhibit a shelf life of nearly one full week. This is in sharp contrast to the four day shelf life typical of prior basil. Such a dramatic increase in shelf life increases the commercial value of 'Maha' as less product is discarded due to wilting or blackening. Further, the product as purchased by the consumer appears fresher and therefore can demand a premium price.

Not only is 'Maha' producing at exceptional levels, but the quality of the harvested plant material is also exceptional. Basil, as a culinary herb, is used primarily for its appealing aroma and unique taste. The new basil plant has a very strong aroma. This very strong anise aroma can be initiated with only a slight brushing of the leaf surface. Indeed, it has even been observed that a light wind blowing across the leaf causes 'Maha' to emit a pleasant aroma. Accompanying this unusally strong and easily produced aroma is an unusally strong basil flavor. The presence of such strong aroma and flavor indicate the presence of increased levels of essential and volatile oils in 'Maha' when compared to levels observed in prior known varieties of basil.

DETAILED DESCRIPTION OF THE INVENTION

The following outline sets forth a number of features 'Maha'. Color specification in parenthesis below were determined by reference to The R.H.S. Colour Chart of The Royal Horticultural Society of London.

Type: A new variety of sweet Italian basil.

Breeding: Asexual reproduction from a plant propagated from Sweet Italian basil seed.

Propagation: Holds its distinguishing characteristics through successive propagation by cuttings.

Habit: Exceptional yield of the 'Maha' is due to the numerous branches, with nodes spaced every three to four inches along the main stem. Each node produces up to five individual leaves. The distance between nodes decreases from the base to the tip of the plant. 'Maha' is sustainable season to season.

Growth: Mature plant reaches an overall height of about two and a half to four feet. The new plant also exhibits dramatically increased growth rates allowing between 15 and 25 harvests per year. The plants are grown on sixteen-inch centers in a plastic-covered greenhouse. They reach a height of two-and-a-half to four feet in about four months from a rooted cutting.

Foliage: Leaves are unusually long with a mature length between three and four inches. The leaves generally measure between two and two and a half inches in width. The leaves are opposite in arrangement and oval in shape with a slight cupping downward not only from the ribs but also interveinal. The texture of the leaf has a slight ripple. Young leaves show no serration on leaf edge but as leaves mature, a slight serration appears as shown in the drawing. The color of the upper surface of the leaf is a light dark green (132C) to a medium dark green (135B).

Main stems: Six to eight branches appear from the main stem. Nodes are spaced three to four inches apart on each stem with four to five shoots per node. The main stem is a light green, a lighter green than the color of the leaves.

Petiole: Approximately 1½ to 2 inches in length and having a light green color that is lighter than the color of the leaves.

Leaves: Approximately 3 to 4 inches in length.

Pubescence: None.

Seed: Tiny dark brown seeds.

Harvesting season: Year round depending on climate. The plant holds yield down to 50° F. and holds yield in excess of 110° F.

Flowers: Flowers are generally white in color and about one-half inch in both length and width. The flowers are generally two-lipped with four lobes and four stamens. They are born in whirls on racemes on top of stems.

Flavor: Stronger anise flavor as compared to previous Sweet Italian basil.

Aroma: Strong anise aroma initiated by only a slight perturbation.

Essential oils: Higher concentration of essential oils as compared to previous Sweet Italian basil.

Disease resistance: Strong resistance to Fusarium wilt.

Pest resistance: Increased resistance to root knot nematode.

Productivity: Yield up to 19,300 pounds per acre per month in summer, and up to 8,950 pounds per acre per month in winter.

Life span: Typical life span of one year. Observed life span up to 18 months.

Use: Used as a culinary herb in either dried or fresh form.

Fresh shelf life: Nearly seven days.

What is claimed is:

1. A new and distinct variety of basil plant, substantially as herein described and illustrated.

* * * * *